United States Patent [19]
Fossel

[11] Patent Number: 5,922,332
[45] Date of Patent: Jul. 13, 1999

[54] TOPICAL DELIVERY OF ARGININE TO OVERCOME PAIN

[76] Inventor: Eric T. Fossel, 17 Sunset View Rd., S. Hero, Vt. 05486

[21] Appl. No.: 08/932,595

[22] Filed: Sep. 17, 1997

[51] Int. Cl.⁶ .............................. A61K 6/00; A61K 7/00
[52] U.S. Cl. .............................................. 424/401; 424/450
[58] Field of Search .............................................. 424/401

[56] References Cited

U.S. PATENT DOCUMENTS

| | | | |
|---|---|---|---|
| 4,681,897 | 7/1987 | Brand | 514/557 |
| 5,595,753 | 1/1997 | Hechtman | 424/436 |

OTHER PUBLICATIONS

Pauly et al., *Chemical Abstracts,* vol. 113 #65069, 1990.

*Primary Examiner*—Thurman K. Page
*Assistant Examiner*—Sharon Howard
*Attorney, Agent, or Firm*—Lorusso & Loud

[57] ABSTRACT

The use of a topical preparation for producing enhanced levels of the precursor of the endogenous analgesic kyotorphin for the purpose of overcoming pain is disclosed. Specifically, use of a topical preparation provides local delivery of the amino acid L-arginine, an important biological precursor to the main substance which is responsible for relaxation of blood vessels permitting enhancement of blood flow. In the preferred embodiments, the L-arginine is provided so that it can be topically applied to the area of pain. The preparation also contains an agent which aids in the transfer of L-arginine into the tissue. In the preferred embodiments this agent overcomes the resistance to transfer caused by the high charge density of L-arginine. In the preferred embodiments this means is high ionic strength created by addition of sodium chloride. Other preparations containing, in addition to L-arginine, substances which overcome pain by other mechanisms such as capsaicin which depletes sensory fibers of substance P constitutes an additional embodiment. These preparations, when topically applied to the area of pain overcomes pain.

10 Claims, No Drawings

TOPICAL DELIVERY OF ARGININE TO OVERCOME PAIN

BACKGROUND

1. Field of the Invention

This invention relates to the use of a topical cream, gel, or other vehicle which contains substances such as L-arginine which delivers these substances into tissue for the purpose of producing beneficial effects such as relief of pain, as well as beneficial effects through a variety of mechanisms such as providing increased levels of natural analgesic kyotorphin and/or restoration of natural mechanisms based on improvement of local blood supply.

2. Prior Art

Approaches to overcoming pain are multiple and consist of oral analgesic agents ranging from aspirin and ibuprophen to more powerful narcotic oral agents such as codeine. Alternatively, in severe pain i.v. administration of agents including such agents as narcotics including morphine are used. Topical agents such as liniments and most recently the agent capsaicin derived from hot peppers have been used with success.

It has been found that the amino acid L-arginine is a precursor to the natural endogenous analgesic substance, kyotorphin. It has been shown that intravenous administration of large amounts (30 g/patient) of L-arginine is successful in overcoming pain. See A. Harima et al. *Europ Neuropsych* 1, 529 (1991). It is thought that this treatment exerts it effect by increasing levels of kyotorphin. However, this treatment is impractical for use in everyday life and is reserved only for the most extreme forms of chronic pain. Others have found that nitric oxide, whose biochemical precursor is L-arginine potentiates b-endorphin-induced pain relief. See L. Tseng et al. *Eur J Pharm* 212, 301 (1992). Still other mechanisms of pain relief from administration of L-arginine may exist.

Pain relief comes from a variety of mechanisms. One which is distinct from those by which L-arginine operates is the depletion of substance P from sensory type C fibers. This has been shown to be effected by application of capsaicin, a substance derived from hot peppers. See B. Mathias et al. *Am J Phys Med & Rehab* 74, 39 (1995).

It was discovered that topical application of the nitric oxide precursor, L-arginine, in its various forms including a variety of topical preparations, either by themselves or with other agents to aid in penetration such as a high ionic strength environment, neutralization of its charge in a complex or by other means, or included in a liposome or other biological carrier, when administered to painful areas of the body can overcome pain in many persons. It was further discovered that such topical preparations described above when fortified with capsaicin or its source extract, oleoresin capsicum, are administered to painful areas of the body can overcome pain in many persons.

In accordance with this invention, a penetrating cream containing L-arginine in a concentration sufficient to produce the desired effect along with sodium chloride or other salts at a concentration sufficient to produce a hostile biophysical environment when applied locally as the cream directly to the painful area was effective in overcoming pain. Further, in accordance with this invention, a penetrating cream containing L-arginine and capsaicin or oleoresin capsicum in concentrations sufficient to produce the desired effect along with sodium chloride or other salts at a concentration sufficient to produce a hostile biophysical environment when applied locally as the cream directly to the painful area was effective in overcoming pain.

Consequently, with the discovery of the present invention, a means to overcome pain has been found.

These and other objects and features of the present invention will become apparent to those skilled in the art from reading the description of the invention, which follows.

SUMMARY OF THE INVENTION

Accordingly, objects and advantages of the instant invention are to provide a means for overcoming pain.

In preferred embodiments, the delivery vehicle is a penetrating cream. In the cream the L-arginine is present as L-arginine hydrochloride alone or with capsaicin or oleoresin capsicum in a concentrations sufficient to produce the desired effect and the agent which creates the hostile biophysical environment is sodium chloride at a concentration sufficient to aid in tissue absorption of the highly charged molecule, L-arginine.

PREFERRED EMBODIMENTS

The preferred embodiment consists of a base cream with the properties of excellent absorption into the skin which also contains L-arginine hydrochloride (12.5% w/v), choline chloride (10% w/v), magnesium chloride (5% w/v) and sodium chloride (5% w/v) alone or with capsaicin (0.025%) or oleoresin capsicum (0.5%). The components of the base cream may be those commonly found in hand creams. The purpose of L-arginine hydrochloride is to provide a precursor to the molecule, nitric oxide, NO. The purpose of the sodium chloride is to provide a high ionic strength environment for the highly charged molecule, L-arginine. The purpose of the capsaicin or oleoresin capsicum is to deplete sensory fibers of substance P. The cream is the agent which is applied to the in order to aid in overcoming pain.

The treatment consists of application of the cream directly to the painful area. When carried out every four hours for a period of 12–16 hrs and then maintained with twice daily administration causes substantial relief from pain.

EXAMPLE 1

In a 52 year old woman with a 13 year history of chronic neck pain administered a penetrating cream containing L-arginine hydrochloride (12.5% w/v), choline chloride (10% w/v), magnesium chloride (5% w/v) and sodium chloride (5% w/v) every four hours for 1 day followed by twice daily administration directly to the neck brought relief from the pain within the first day. This relief of symptoms was maintained by continuation of the twice daily treatment.

EXAMPLE 2

In a 35 year old man with a three year history of shoulder pain applied a penetrating cream containing L-arginine hydrochloride (12.5% w/v) and choline chloride (10% w/v), magnesium chloride (5%), sodium chloride (5%) and oleoresin capsicum (0.5%) every four hours for 1 day followed by twice daily applications directly to the painful area. Relief from pain was obtained within 8 hours. The relief of symptoms was maintained by continuation of twice daily treatments.

Other Embodiments
Other active agents

While L-arginine hydrochloride is the preferred active agent because it is the agent in nature itself, it is non-toxic, is highly soluble and it is inexpensive, other agents could be used which are also precursors or donors of nitric oxide. These include the salt, arginine glutamate, the salt, arginine butyrate, and esters of arginine such as arginine ethyl ester or arginine butyl ester as well as other donors of nitric oxide.

In the case an alternative active agent were used it would be simply substituted for L-arginine in a delivery preparation and the preparation used as in the case of the L-arginine preparation. The cream may contain capsaicin or oleoresin capsicum in addition to L-arginine.

Other means of effecting absorption

A variety of means for effecting absorption of the active agent from the topical cream might be envisioned. One principle behind the absorption of a highly charged molecule such as L-arginine into tissue is to either create a biophysically hostile environment in the delivery vehicle such that L-arginine would prefer to be in tissue, or to package L-arginine in such a way that it is carried into tissue or neutralize its charge by derivitization or forming a neutral salt. Examples of biophysically hostile environments, include but are not limited to, high ionic strength, high or low pH, and highly hydrophobic environments. Examples of packaging which would be carried into tissue includes liposomes or emulsions of collagen, collagen peptides or other components of skin or basement membrane. Examples of neutralization of charge include the salt, arginine glutamate which is electronically neutral.

In each case of creating a hostile biophysical environment for the active agent, the agent was added to an appropriate preparation. In the case of creating a high ionic strength ions such as but not limited to sodium chloride, potassium chloride, choline chloride, lithium chloride, alone or in combination were added in high concentration. Other highly charged molecules such as polylysine, polyglutamine, polyaspartate or copolymers of such charged amino acids may be used to create the hostile biophysical environment. Alternatively a hostile biophysical environment may be created by placing the highly charged L-arginine in an hydrophobic, oily environment such as in an oil-based cream containing little or no water. Absorption may further be aided by combining the use of hostile biophysical environments with the use of penetrating agents such as molecules containing heterocyclic rings to which are attached hydrocarbon chains.

It can be seen that in the present invention I have provided a method and agents which when applied to a person with pain causes overcoming of pain by use of the body's own mechanisms. This effect is achieved by providing the biochemical substrate at the local site from which the controlling substance, L-arginine causes enhancement in levels of the natural analgesic kyotorphin and/or enhancement of the effectiveness of natural endorphins. Further, it is seen in the present invention when L-arginine is used in conjunction with capsaicin or oleoresin capsicum, an additional mechanism of pain relief, depletion of substance P from sensory fibers is activated.

Although the description above contains many specificities, these should not be construed as limiting the scope of the invention but as merely providing illustrations of some of the presently preferred embodiments of this invention. Various other embodiments and ramifications are possible within this scope.

Thus the scope of the invention should be determined by the appended claims and their legal equivalents, rather than by the examples given.

What is claimed is:

1. A method of overcoming pain comprising delivering a kyotorphin releasing substance selected from a member of the group consisting of L-arginine, L-arginine salts and L-arginine derivatives, to skin comprising the step of topically applying to the skin a vehicle containing an effective amount of the substance, and a concentration of ionic salt sufficient to create an ionic environment which causes the substance to migrate from the vehicle to the skin where the substance is absorbed in conjunction with delivering a P depleting agent selected from a member of the group consisting of capsaicin and oleoresin to the skin.

2. The method of claim 1 wherein a topical delivery vehicle selected from the group consisting of topical creams, topical liquids, topical lotions and topical ointments containing the substance, the ionic salt and the P depleting agent is applied to the skin.

3. The method of claim 1 wherein a hydrophobic delivery vehicle containing the substance, the ionic salt and the P depleting agent is applied to the skin.

4. The method of claim 1 wherein a vehicle containing the substance and the P depleting agent within a liposome, and the ionic salt is applied to the skin.

5. The method of claim 1 wherein a vehicle containing the substance and the P depleting agent within a liposome and an ionic salt concentration sufficient to create an ionic strength environment within the liposome is applied to the skin so that the liposomes migrate from the vehicle to the skin.

6. The method according to any of the preceding claims wherein the delivery vehicle, the substance and the P depleting agent is contained in a condom which is placed on the penis.

7. The method of claim 1 wherein a transdermal patch containing the substance, the ionic salt and the P depleting agent is applied to the skin.

8. The method of claim 1 wherein a delivery vehicle comprising water (20–80%), mineral oil (3–18%), glyceryl stearate (0.25–12%), squalene(0.25–12%), cetyl alcohol (0.1–11%), propylene glycol stearate (0.1–11%), wheat germ oil (0.1–6%), polysorbate 60 (0.1–5%), propylene glycol (0.05–5%), collagen (0.05–5%), sorbitan stearate (0.05–5%), vitamin A&D (0.02–4%), vitamin E (0.02–4%), triethanolamine (0.01–4%), methylparaben (0.01–4%), aloe vera extract (0.01–4%), imidazolidinyl urea (0.01–4%), propylparaben (0.01–4%), bha (0.01–4%), L-arginine hydrocholide (0.25% to 25%), sodium chloride (0.25% to 25%), the substance and the P depleting agent is applied to the skin.

9. The method of claim 1 wherein a delivery vehicle consists of capsaicin as a P depleting agent in the range from 0.005 to 0.5% w/v.

10. The method of claim 1 wherein a delivery vehicle consists of oleoresin as a P depleting agent in the range from 0.05 to 2.5% w/v.

* * * * *